United States Patent
Voigt et al.

(10) Patent No.: US 6,306,306 B1
(45) Date of Patent: *Oct. 23, 2001

(54) CHROMATOGRAPHIC PROCESS FOR OBTAINING HIGHLY PURIFIED CYCLOSPORIN A AND RELATED CYCLOSPORINS

(75) Inventors: Ulrich Voigt, Dresden; Joachim Kinkel, Guldental; Roland Hempel, Mobschatz/Dresden, all of (DE); Roger-Marc Nicoud, Richardsmenil (FR)

(73) Assignee: Arzneimittelwerk Dresden, Radebeul (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/821,823

(22) Filed: Mar. 21, 1997

(30) Foreign Application Priority Data

Mar. 21, 1996 (DE) .............................. 196 11 094

(51) Int. Cl.[7] .................................. B01D 15/08

(52) U.S. Cl. .................. 210/635; 210/659; 530/317; 530/321; 530/413; 530/417

(58) Field of Search ................... 210/635, 656, 210/659, 198.2, 502.1; 530/317, 321, 413, 417

(56) References Cited

U.S. PATENT DOCUMENTS

| | | | |
|---|---|---|---|
| 4,117,118 | 9/1978 | Härri et al. | 424/177 |
| 4,215,199 | 7/1980 | Härri et al. | 435/71 |
| 4,288,431 | 9/1981 | Traber et al. | 424/177 |
| 5,382,655 | 1/1995 | Szanya et al. | 530/317 |
| 5,709,797 | * 1/1998 | Bocchiola | 210/635 |

FOREIGN PATENT DOCUMENTS

| | | | |
|---|---|---|---|
| 2096892 | 11/1993 | (CA) | 210/635 |
| 2 227 489 | 8/1980 | (GB) | 210/635 |
| 0 568 698 | 11/1993 | (GB) | 210/656 |
| WO 92/13094 | 8/1992 | (WO) | 210/635 |

OTHER PUBLICATIONS

Charto et al., "Complete Design of a Simulated Moving Bed," Journal of Chromatography A. 702, 1995, pp. 97–112.

Nicoud et al., "Simulated Moving Bed Licosep 12/26," Separex Chimie Fine (Brochure), 1993, 2 pages.

Küsters et al., "Enantioseparation of a Chiral Epoxide by Simulated Moving Bed Chromatography using Chiralcel-1–OD," Chromatographia, vol. 40, No. 7/8, Apr. 1995, pp. 387–394.

Isaksson et al., A Packing Procedure Suitable for High Flow Rate and High Stability Columns Using Cellulose Triacetate, LC–GC INT. vol. 6, No. 10, Oct. 1993, pp. 636–637.

"CAD/CAM/CAE im Apparate–und Behälterbau," Chem.–Ing.–Tech. 63, 1991, Nr. 9, p. A 536.

"Le Licosep, A Continuous Chromatographic Process with Low Dilution (Simulated Moving Bed)," Separex Chimie Fine (Brochure) (Undated) pp. 1–11.

(List continued on next page.)

Primary Examiner—Ernest G. Therkorn
(74) Attorney, Agent, or Firm—Pillsbury Winthrop LLP

(57) ABSTRACT

The present invention relates to a novel chromatographic process which is suitable for the purification of cyclosporin-containing crude extracts on industrial scale. In this process, the conventional preparative chromatographic separation methods are completely or at least partially replaced by the simulated moving bed method (SMB). The cyclosporin A obtained corresponds both to the quality requirements of USP XXIII and of EUROPEAN PHARMACOPOEIA, 2nd Edition 1995.

9 Claims, 5 Drawing Sheets

OTHER PUBLICATIONS

Nicoud et al., Preparative Scale Enantioseparation of a Chiral Epoxide: Comparison of Liquid Chromatography and Simulated Moving Bed Adsorption Technology, Chirality 1993, 5, pp. 267–271.

Schmidt–Traub et al., "Dynamic Simulation of Simulated–Moving–Bed Chromatographic Processes, " Computers chem. Engng vol. 20, Suppl., 1996, pp. S641–S647.

Schmidt–Traub et al., "Dynamic Simulation of Simulated–Moving–Bed Chromatographic Processes," Computers chem. Engng vol. 22, No. 9, 1998, pp. 1309–1317.

Blehaut et al., "Separation of Fatty Alcohol Stereoisomers on a Large–Scale High–Performance Simulated Moving Bed," LC–GC International, Apr. 1996, pp. 228–238.

Nicoud et al., "Simulated Moving Bed (S.M.B.): Applications for Enantiomer Separations on Chiral Stationary Phases," in Simulated Moving Bed Basics and Applications, 1993, ed. R. M. Nicoud, pp. 65–88, ISBN 2–905–267–21–6.

Schulte et al., "Simulierte Gegenstromchromatographie—eine effiziente Technik zur Herstellung optisch aktiver Verbindungen im industriellen Maβstab*," Chemie Ingenieru Technik (68), 1996, 86 (6), pp. 670–683.

Bailly et al., "The simulated moving bed: a powerful process for purification",Biotechnology of Blood Proteins. Eds C. Rivat, J.–F. Stolz. Colloque INSERM/John Libbey Eurotext Ltd., 1993, vol. 227, pp. 13–18.

Nadler et al., "Continuous Purification of Proteins by Selective Nonadsorptive Preparative Chromatography,", American Chemical Society, Symp. Ser. 1993, 529, pp. 14–26.

Shuji Adachi et al., Separation of Peptide Groups with Definite Characteristics from Enzymatic Protein Hydrolysate, Agricultural and Biological Chemistry, Apr. 1991, pp. 925–935, vol. 55.

Abstract, 16–Fermentations, p. 561, vol. 119, 1993, 224320.

* cited by examiner

Cyclosporin A - crude extract

| 1st chromatographic stage | Silica gel Si 60 | |
|---|---|---|
| conventional preparative HPLC | Ethyl acetate | |
| | | |
| | Useful fraction 1 | Useful fraction 2 |
| | Non-polar | Polar |
| | Cy A+Cy G, Cy D etc. | Cy A+Cy L, Cy U etc. |

| 2nd chromatographic stage | Si 60 | |
|---|---|---|
| SMB | Ethyl acetate | Ethyl acetate |

FIG. 3

Cyclosporin A crude extract

| 1st chromatographic stage | Silica gel Si 60 |
|---|---|
| Conventional preparative HPLC | Ethyl acetate |
|  |  |
|  | Useful fraction 1 | Useful fraction 2 |
|  | Non-polar | Polar |
|  | Cy A+Cy G, Cy D etc. | Cy A+Cy L, Cy U etc. |

| 2nd chromatographic stage | RP-18 | Si 60 |
|---|---|---|
| SMB | Acetonitrile/water | Ethyl acetate |
|  |  |  |
|  |  | or |
|  |  | after exchanging the extract/raffinate position: |
|  |  | RP-18, acetonitrile/water |

Cyclosporin A crude extract

| 1st chromatographic stage SMB | Si 60 Ethyl acetate | |
|---|---|---|
| | Raffinate | Extract |
| | Cy A+non-polar impurities | Concentration of the polar impurities (Example 1) |

| 2nd chromatographic stage SMB | RP-18 Acetonitrile/water | |
|---|---|---|
| | Raffinate | Extract |
| | Cy A | Concentration of the non-polar impurities (Example 2) |

CHROMATOGRAPHIC PROCESS FOR OBTAINING HIGHLY PURIFIED CYCLOSPORIN A AND RELATED CYCLOSPORINS

BACKGROUND OF THE INVENTION

1. Field of the Invention

The present invention relates to a novel process for the chromatographic purification of cyclosporin A (Cy A) and related cyclosporins, which is suitable for use in the pharmaceutical industry.

In this process, the active compounds are obtained in a pharmaceutically acceptable purity under economically favourable conditions, i.e. in the case of cyclosporin A, for example, the purity requirements of PHARMEUROPA (PHARMEUROPA Vol. 4, No. 4, page 270, December 1992) are fulfilled.

2. Background Information

With the successful isolation of cyclosporin A from Trichoderma polysporum (LINK ex PERS.) Rifai by A. R üegger and co-workers [Helv. Chim. Acta 59, 112, (1976)], for the first time a novel, strongly immunosuppressant class of substance was available. In the meantime, as a result of intensive investigations more than 25 related cyclosporins having immunosuppressant and antifungal activity became known [R. Traber et al. Helv. Chim. Acta 70, 13 (1987)]. Today, the outstanding importance of cyclosporin A as the agent of choice in the suppression of the immune defence after organ transplantations is undisputed. As a result of this, in the past there has been no lack of efforts to fulfil the continuously increasing requirements with respect to amount and quality for this lifesaving pharmaceutical by improvement of the preparation process.

The technical solutions known until now for the purification of cyclosporin A-containing crude extracts mostly comprise a plurality of chromatographic stages using organic solvents as eluents.

Thus in the abovementioned study of A. Rüegger, chromatography was first carried out on silica gel 60 Merck (0.063–0.2 mm) with chloroform in increasing amounts of methanol. The product obtained was subsequently subjected to gel chromatography on Sephadex LH 20 in methanol and then finally chromatographed on alumina (Brockmann, Act. I) in toluene with increasing amounts of ethyl acetate.

Later studies also make use of a similar procedure (Table 1). The absorbents Sephadex LH 20, silica gel 60 Merck (0.063–0.2 mm) and neutral alumina are frequently used.

The eluents employed are mostly mixtures of organic solvents.

On account of their high toxicity, chloroform and methylene chloride are unsuitable here, both with respect to solvent residues remaining in the active compound and also because of the safety problems resulting therefrom in the processing of relatively large amounts of these substances (distillation, disposal).

Furthermore, when using gradients or complicated, for example ternary, isocratic mixtures a new adjustment of the eluents after distillation of the eluates is troublesome and expensive.

A method described by BIOGAL in Canadian Patent CA 2 096 892, in which the crude extract is subjected to temperature treatment before chromatography, is also to be assessed similarly.

The crude product is heated at about 110° C. here for about 1 hour and subsequently cooled to room temperature over the course of 5 hours under defined conditions. Using a high proportion of chlorinated hydrocarbons, about 15% of the applied amount of cyclosporin A is isolated in a purity of about 97.6% in single-stage chromatography on silica gel 60 in two eluent systems employed in succession. These results, however, may not be satisfactory with respect to industrial use, as regards yield and purity of the active compound obtained. Additionally, experience shows that these complicated natural substances should not be exposed to any temperature stress because of their thermal instability and possible isomerization.

According to the present state of knowledge, only the applications of FUJISAWA (WO 9 213094) and BIOGAL (CA 2 096 892) manage with single-stage chromatographic purification. To do this, however, a complicated eluent combination or a gradient is necessary, which makes eluent regeneration more difficult.

For more accurate assessment of this method, however, details concerning yields and product purities achieved are mostly lacking.

Examples of some presently known chromatographic purification methods for cyclosporin A

| Patent | Company | Purification steps |
|---|---|---|
| US 4 117 118 | SANDOZ | 1. Sephadex LH 20, methanol |
| | | 2. Neutral alumina, toluene/ethyl acetate, gradient |
| | | 3. Silica gel 60, chloroform/methanol 98:2 |
| US 4 215 199 | SANDOZ | 1. Silica gel 60, chloroform/methanol 98:2 |
| | | 2. Sephadex LH 20, methanol |
| | | 3. Silica gel 60, chloroform/methanol 98:2 |
| BE 879 402 | SANDOZ | 1. Sephadex LH 20, methanol |
| | | 2. Silica gel 60, hexane/acetone 66:33 |
| | | 3. Crystallisation, acetone, −15° C. |
| WO 9 213 094 | FUJISAWA | 1. Silica gel, hexane Hexane/ethyl acetate, gradient Acetone |
| GB 2 227 489 | BIOGAL | 1. Silica gel 60, chloroform/methanol/acetone 92:4:4 |
| | | 2. Silica gel 60, hexane/acetone, gradient |
| CA 2 096 892 | BIOGAL | 1. Silica gel 60, chloroform/dichloromethane/ethanol 48:50:2 Chloroform/ethyl acetate/ethanol 48:50:2 |

A brief description of the SMB technique per se is found, for example, in R. M. Nicoud, LC-GC INTL Vol. 5, No. 5, 43–47 and K. K. Unger (Ed.), Handbuch der HPLC [HPLC Handbook], Part 2, GIT Verlag, Darmstadt, 1994. (see FIG. 1)

SUMMARY OF THE INVENTION

Starting from the prior art outlined here, the following objectives result for an inventive solution to the chromatographic purification of cyclosporin A with high requirements for product purity and yield:

The new procedure should yield more than 70% of the amount of cyclosporin A employed with a quality corresponding to PHARMEUROPA (based on the chromatographic purification steps).

The procedure should meet the highest requirements with respect to annual throughput and at the same time drastically reduce the need for solvents and materials for the stationary phases.

The technical solution should be simple, rapid and robust, i.e. solvents and adsorbents must be reusable over a period which is as great as possible. Thus the use of solvent mixtures and gradients, used isocratically, which are difficult to adjust or regenerate is also inapplicable.

Chlorinated hydrocarbons should not be used.

The process should offer possibilities for automation, i.e. for continuous operation, and at the same time meet the requirements of production complying with GMP.

The starting material used for the chromatographic purification is, for example, a crude extract obtained according to known methods (e.g. DD 295 872 A5) from cyclosporin A-containing dried mycelium by extraction (ethyl acetate) and defatting (petroleum spirit/methanol/water), which besides a number of mostly unknown yellow- and red-coloured substances and oily products, for example, has the following composition of cyclosporins:

| Cyclosporins | Unstandardized relation %[1) |
|---|---|
| C | 14.9 |
| B | 13.7 |
| L | 0.2 |
| A | 65.1 |
| G | 1.2 |
| D | 1.2 |
| Other | 3.7 |

[1)]HPLC analytical determination according to PHARMEUROPA Vol. 4, No. 4, 270 ff.

In a first chromatography step, the polar cyclosporins (C, B, L, U) are separated from the non-polar cyclosporins (G, D) such that two useful fractions result, which besides cyclosporin A either contain only polar or only non-polar impurities. By this means, in the second chromatographic stage cyclosporin A can advantageously be purified from the respective impurities.

According to the invention, the ultrapurification of cyclosporin A is carried out by means of chromatographic purification by use of conventional HPLC in combination with the simulated moving bed technique (SMB) as follows:

1st chromatography HPLC or SMB technique
2nd chromatography SMB technique
See Schemes 1–4.

Put more precisely, the invention relates to a process for the purification of cyclosporin A and related cyclosporins from a cyclosporin-containing crude extract using chromatographic processes with silica gel as adsorbent, which is distinguished in that a) in a first chromatographic stage, the crude extract is separated by fraction cuts in the separated concentration profile into a useful fraction 1 containing the non-polar concomitants and into a useful fraction 2 containing the more polar concomitants by means of preparative HPLC or SMB technique and b) the useful fraction 1 (raffinate) and the useful fraction 2 (extract) are subjected to a subsequent second chromatographic stage by means of SMB technique. It is possible here for both the first chromatographic stage and the second chromatographic stage to be carried out in the normal-phase system ethyl acetate or reverse-phase system acetonitrile/water.

In particular, the following advantages are achieved by the use of the SMB technique:

An absolutely continuous procedure can be realised, i.e. by means of the new chromatographic mode discrete substance injections are unnecessary. Continuously operating chromatography of this type is especially advantageous for industrial use.

The SMB technique makes it possible to work with more concentrated solutions than before. As a result, the solvent requirement falls and with it, at the same time, also the time needed for solvent recovery.

| • Efficacy of SMB in coparision with HPLC-technique | | |
|---|---|---|
| Pasesystem | Parameter | Quotient (SMB:HPLC) |
| Normal-phase system | Use of ethyl acetate | 0.7 |
| | Use of Si 60 material | 0.25 |
| | Productivity (g of feed/day/kg of adsorbent) | 2.5 |
| Reverse-phase system | Use of acetonitrile/ water | 0.15 |
| | Use of RP-18 material | 0.15 |
| | Productivity (g of feed/day/kg of adsorbent) | 10 |

The most important technical requirement for the realization of an SMB separation is the accurate adjustment of the various individual flows (see examples), in order to guarantee the quasi-stationary state of the elution fronts as a function of the switching times.

Furthermore, an accurate knowledge of the adsorption isotherms of the useful product and of the impurities in the chromatographic system used is necessary for the optimum adjustment of the SMB separation. These must be determined analytically beforehand.

It was furthermore possible, by introduction of a so-called fifth zone, to abandon the hitherto customary two-component separation of the classical four-zone SMB. By means of the washing system installed in this additional zone, the elimination of impurities which have extreme k' values with respect to cyclosporin A is now also possible in the same run. A further quality improvement in the useful product is thus possible. Customarily, using the standard SMB technique mixtures having k' values of between 0.6 and 2.0 can mostly be readily separated (k'=1 stands for the useful product). However, components which lie outside this range are normally only incompletely washed out in the extract, so that concentration in the raffinate in comparison with the feed occurs (FIG. 1).

In the novel procedure according to the invention, the columns are brought into a defined state by washing with a solvent of strong eluting power (e.g. methanol) on switching between the fourth and the first zone. The columns of the apparatus concerned, which are located in this fifth zone, are then completely disconnected from the closed ring unit of the other four zones for the duration of one cycle (FIG. 1).

This fifth zone is subdivided here into two individual steps:

1. During the period of the first individual step, the columns of the fifth zone are washed with a suitable solvent of high eluting power in order to clean the stationary phase of still adhering impurities.

The rinsing agent used is preferably methanol. In the case of rinsing of the RP material, pure acetonitrile can also be employed, whereby the problem of solvent recovery is simplified by the lack of necessity for an additional solvent.

2. In the second individual step, rinsing is changed from the rinsing agent to the eluting agent necessary for the particular separation.

If the columns are distributed in the zones such that a plurality of columns are located in the fifth zone, the rinsing process can be intensified if these columns are connected in parallel during the rinsing.

A further optimization of the procedure was achieved in the ultrapurification of the so-called useful fraction 2 of the first chromatographic stage. Besides cyclosporin A, this fraction especially contains the more polar impurities, such as cyclosporin U and L. It was surprisingly found here, after exchanging the withdrawal site for extract and raffinate on the SMB plant, that afterwards this useful fraction 2 can be very easily separated. In this connection, the polar impurities are eluted before the useful product cyclosporin A, i.e. they have shorter retention times. This means that, when using this special SMB regime in the second chromatographic stage, it is then possible to work exclusively with the RP-18 system in this stage, whereby the solvent recovery is greatly simplified (Scheme 2).

BRIEF DESCRIPTION OF THE DRAWINGS

FIGS. 2, 3, 4, and 5 show four schemes for purifying cyclosporin A.

DETAILED DESCRIPTION OF THE INVENTION

The following three examples, confirm the suitability of the SMB technique.

In Example 1, the ultrapurification of an intermediate by means of SMB technique in normal-phase system the silica gel Si 60 ethyl acetate is demonstrated. Besides cyclosporin A, the product employed contains mainly impurities of greater polarity.

The marked depletion of the polar cyclosporins (in particular U and L and also B and C) is to be noted in the results, whereby the suitability in principle of the separation system in combination with the SMB technique is clarified.

Example 2 describes the ultrapurification of an intermediate which, as useful fraction 1, contains mainly non-polar impurities, by means of SMB technique in the RP-18 reverse-phase system acetonitrile/water (60:40, v/v). After the SMB separation, a marked depletion of the non-polar cyclosporins (in particular G and D) is to be observed. At the same time, the higher efficiency of this phase system is demonstrated, using this example, both by the high final purity and by the high content of cyclosporin A achieved after drying.

Example 3 describes the ultrapurification of an intermediate, which contains mainly non-polar impurities, by means of SMB technique in the normal-phase system silica gel ethylacetate. In contrast to example 1 a marked depletion of the non-polar impurities as well as a depletion of consumption of solvents are achieved by exchanging the raffinate positions.

The cyclosporin A obtained corresponds after recrystallisation both to the quality requirements of USP XXIII and EUROPEAN PHARMACOPOEIA, 2nd Edition 1995.

This fine separation is surprising inasmuch as until only years ago, even by means of analytical HPLC, it was not possible to separate these chromatographically extremely similar impurities from cyclosporin A.

Figure 1:
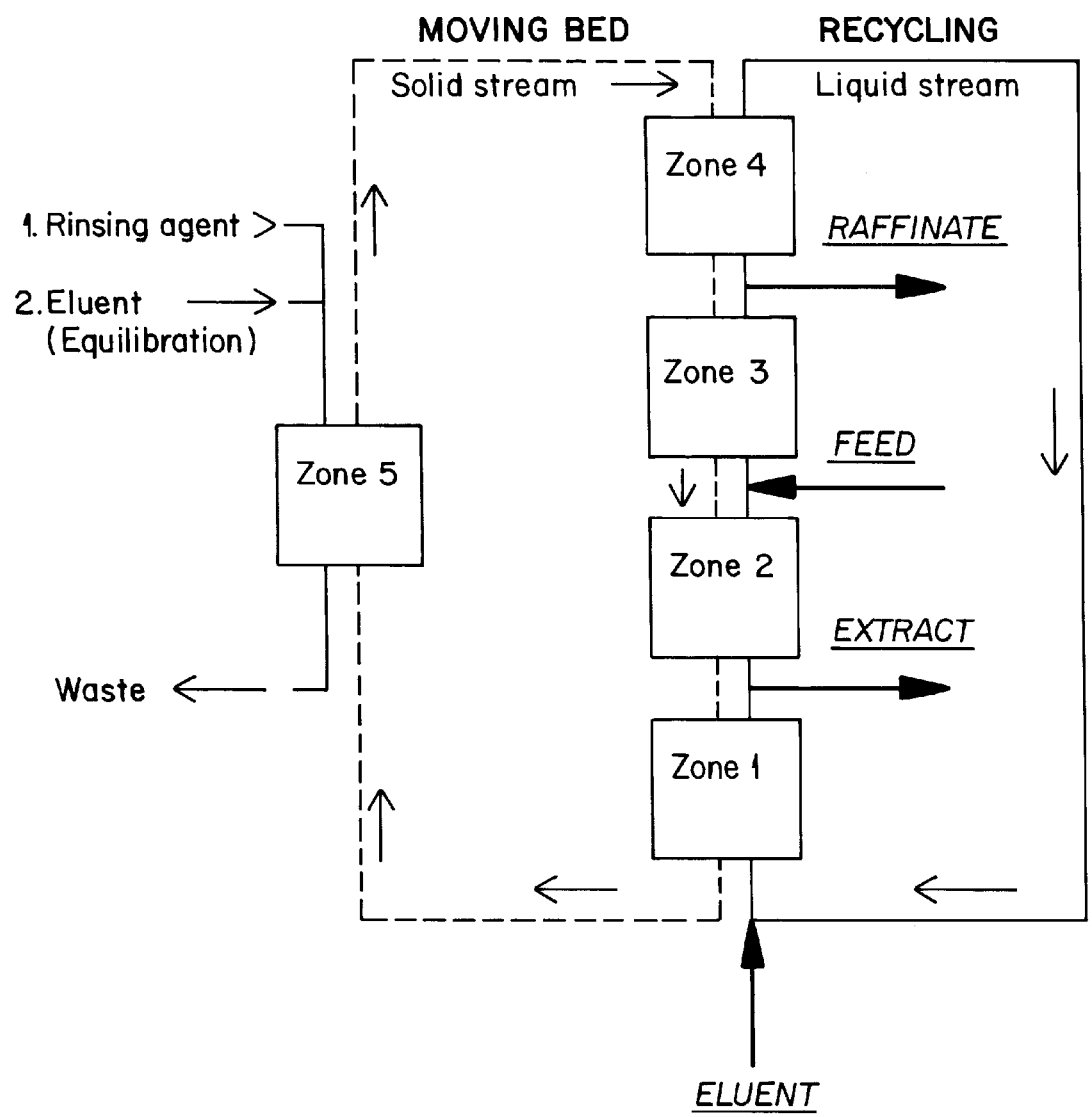
FIG. 1 shows a diagrammatic scheme of a 5 zone simulated moving bed.
Figure 2:
Figure 2:
Figure 2:
Figure 4:
Figure 4:
Figure 5:
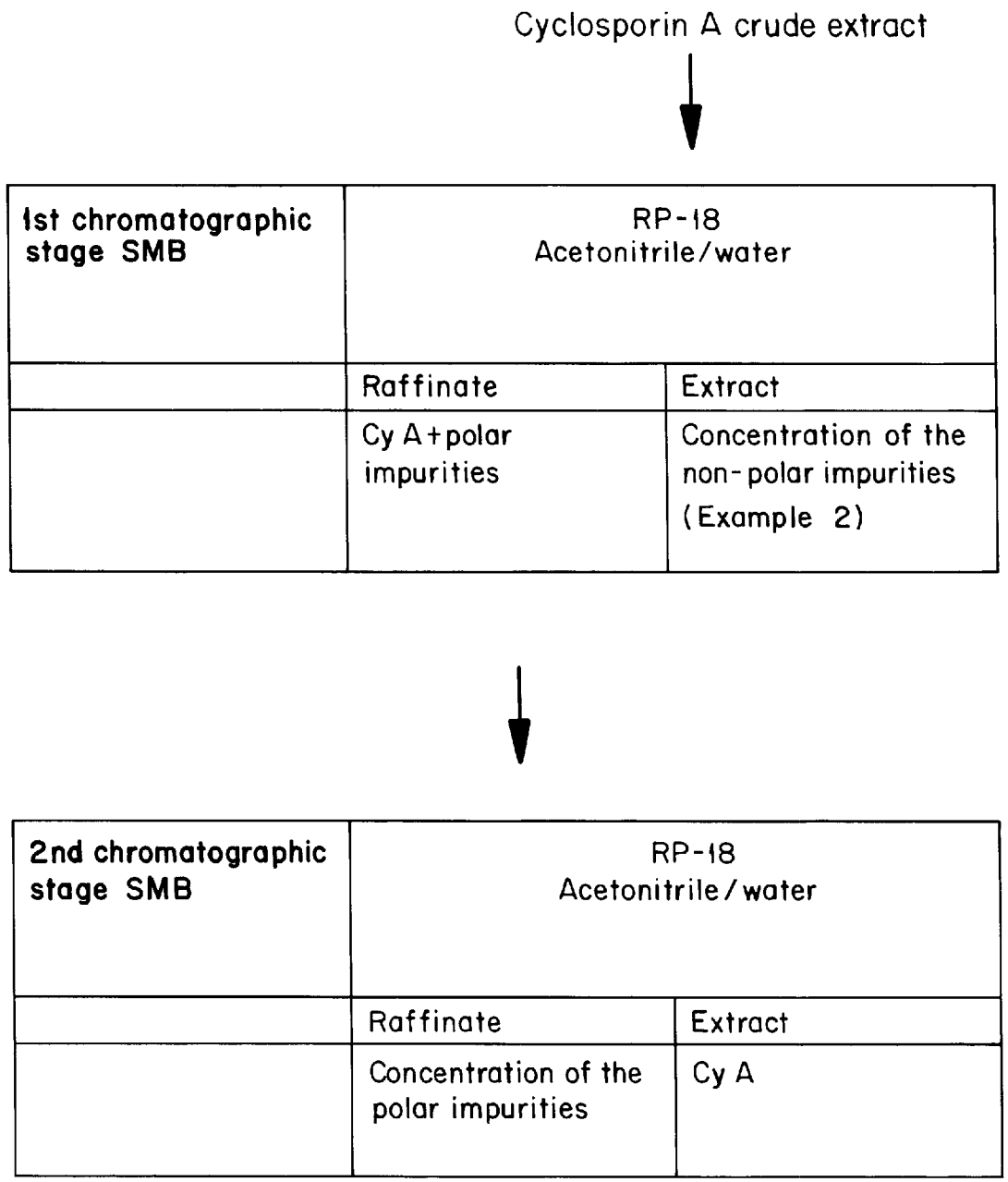

Description of FIG. 1

The eluent is circulated between zones 1 and 4. Sample feed takes place between zones 2 and 3. Fresh eluent is added between zones 4 and 1. Raffinate (cyclosporin A) is withdrawn between zones 3 and 4 and extract (cyclosporin A+impurities) between zones 1 and 2. In the integrated system, each column is provided with four valves for feed (substance feed), eluent, extract (useful product+impurities) and raffinate (useful product). The "movement" of the support material is simulated by moving the collection and feed points against the direction of elution. By this means, a continuous distribution of substance between the phases in the column system can be achieved and the eluate concentrations at the withdrawal points appear constant.

Furthermore, it was surprisingly found in the experimental test that the separation of the secondary cyclosporins U and L, on the one hand, and G and D, on the other hand, by the SMB technique takes place more completely than by conventional chromatography and at the same time higher yields can be achieved in the stages. As a result of this, for comparable productivities smaller plants are possible, which thus have less need both for column packing material and for eluent.

Of course, in principle use of the SMB technique is possible even in the first chromatographic stage (Schemes 3 and 4). In principle the SMB separation can be carried out in the reverse-phase system acetonitrile/water in the presence of suitable crude extracts (low loading with inert materials, especially of lipophilic nature) even in the first stage (Scheme 4). Since, as has been furthermore found, impurities of greater polarity can also be separated in the reverse-phase system acetonitrile/water after exchanging the raffinate/extract positions of cyclosporin A, it is then also possible to carry out the cyclosporin A purification in two stages by means of SMB technique, only using the reverse-phase system acetonitrile/water.

In the same way it is also possible to separate non-polar impurities in the normal-phase system silica gel Si 60 ethylacetate by means of SMB technique after exchanging the raffinate/extract positions. Consequently, it is than also possible to carry out the cyclosporion A purification in two stages by means of SMB technique only using the normal-phase system silica gel ethylacetate

EXAMPLE 1

Separation of mainly polar cyclosporins (cyclosporins C, B, L, U) from cyclosporin A with the aid of the SMB technique in the normal-phase system ethyl acetate.

| Plant | LiChrosep ® 8–50, pilot plant | | |
|---|---|---|---|
| Column | 8 columns, length 100 mm x 50 mm internal Ø, axial compression | | |
| Stationary phase | LiChrospher ® Si 60, 15 µm | | |
| Mobile phase | Ethyl acetate | | |
| Crude substance | # 011194 | Cyclosporins | Purity [%] |
| | | C | 2.3 |
| | | B | 6.9 |
| | | L | 0.7 |
| | | U | 1.2 |
| | | A | 86.2 |
| | | G | 1.0 |
| | | D | 0.1 |

|   |   |   |
|---|---|---|
|   | Sum of the impurities | 13.8% |
| Substance feed | Solution in ethyl acetate 5.8 g/l |   |
| Feed | 5.3 ml/min |   |
| Eluent | 100 ml/min |   |
| Recycling | 151 ml/min |   |
| Detection | HPLC analysis in the extract and raffinate stream |   |
| Results |   |   |
| Raffinate | Cyclosporins | Purity [%] |
|   | C | 0.2 |
|   | B | 0.4 |
|   | L | 0.0 |
|   | U | 0.4 |
|   | A | 97.4 |
|   | G | 1.1 |
|   | D | 0.1 |
|   | Sum of the impurities | 2.6% |
|   | Yield, cyclosporin A: | >95% |
| Extract | Cyclosporin A | 75.5% |
|   | Sum of the impurities: | 24.5% |

The result of the experiment shows the possibility in principle of separating especially the polar impurities from cyclosporin A in the Si 60 system ethyl acetate.

EXAMPLE 2

Separation of mainly non-polar cyclosporins cyclosporins G, D) from cyclosporin A with the aid of the SMB technique in the RP-18 system acetonitrile/water.

|   |   |   |
|---|---|---|
| Plant | LiChrosep ® 8–50, pilot plant |   |
| Column | 8 columns, length 100 mm × 50 mm internal Ø, axial compression |   |
| Stationary phase | LiChrospher ® RP-18, 15 µm |   |
| Mobile phase | Acetonitrile/water - 60/40 - v/v |   |
| Crude substance | # 251094 Cyclosporins | Purity [%] |
|   | L | 0.3 |
|   | U | 0.8 |
|   | A | 92.5 |
|   | G | 4.1 |
|   | D | 1.6 |
|   | Sum of the impurities | 7.5% |
| Substance feed | Solution in acetonitrile |   |
| Feed | 1 g/l |   |
|   | 12.7 ml/min |   |
| Eluent | 81 ml/min |   |
| Recycling | 151 ml/min |   |
| Detection | HPLC analysis in the extract and raffinate stream |   |
| Results |   |   |
| Raffinate | Cyclosporins | Purity [%] |
|   | Unknown (α = 3.4) | 0.1 |
|   | L | 0.2 |
|   | U | 0.5 |
|   | A | 99.1 |
|   | G | 0.0 |
|   | D | 0.0 |
|   | Unknown (α = 20.1) | 0.1 |
|   | Sum of the impurities | 0.9% |
|   | Content, cyclosporin A (dry matter): | 99.4% |
|   | Stage yield of cyclosporin A | >95% |

The results show the possibility of separating the non-polar impurities from cyclosporin A in the RP-18 system acetonitrile/water (60/40, v/v).

EXAMPLE 3

Separation of mainly non-polar cyclosporins (cyclosporins C, G, D) from cyclosporin A in the second chromatography with the aid of the SMB technique in the normal-phase system ethyl acetate after exchanging the raffinate/extract positions.

|   |   |   |
|---|---|---|
| Plant | LiChrosep ® 12–26, pilot plant |   |
| Column | 8 columns, length 100 mm × 26 mm internal Ø, axial compression |   |
| Stationary phase | LiChrospher ® Si 60, 15–25 µm |   |
| Mobile phase | Ethyl acetate |   |
| Crude substance |   | Cyclosporins Purity [%] |
|   | C | 0.04 |
|   | B | 0.122 |
|   | L | 0.075 |
|   | A | 92.462 |
|   | G | 2.934 |
|   | D | 4.177 |
|   | Sum of the impurities | 7.538% |
| Substance feed | Solution in ethyl acetate 28 g/l |   |
| Feed | 1.5 ml/min |   |
| Eluent | 16.4 ml/min |   |
| Detection | HPLC analysis in the extract and raffinate stream |   |
| Results |   |   |
| Extract | Cyclosporins | Purity [%] |
|   | C | 0.02 |
|   | B | 0.075 |
|   | L | 0.063 |
|   | A | 99.364 |
|   | unknown | 0.219 |
|   | G | 0.175 |
|   | Sum of the impurities | 0.636% |
|   | Yield, cyclosporin A: | >95% |

The result shows that the separation of non-polar impurities is also possible in the normal-phase system silica gel Si 60 ethyl acetate by means of SMB technique. However, in this case the exchange of the raffinate/extract positions is necessary, as described above.

What is claimed is:

1. A process for the purification of cyclosporin A and related cyclosporins from a cyclosporin-containing crude extract using chromatographic processes with silica gel as adsorbent, wherein
    a) in a first chromatographic stage, the crude extract is separated by fraction cuts in the separated concentration profile into a useful raffinate fraction 1 containing the non-polar concomitants and a useful extract fraction 2 containing the more polar concomitants by means of preparative HPLC or simulated moving bed technique; and
    b) the useful raffinate fraction 1 and the useful extract fraction 2 are subjected to further separation in a subsequent second chromatographic stage by means of simulated moving bed technique.

2. The process according to claim 1, wherein by means of introduction of a fifth zone, a rinsing step is carried out first with an alcohol and then with the eluent, and wherein with a plurality of columns in the fifth zone these are flowed through in parallel.

3. The process according to claim 1, wherein
    a) both the first chromatographic stage and the second chromatographic stage are carried out in a normal-phase system ethyl acetate or a reverse-phase system acetonitrile/water,
    b) useful raffinate fraction 1 is subjected by means of simulated moving bed technique in a reverse-phase system acetonitrile/water to a second chromatographic stage and useful extract fraction 2 is subjected to a second chromatographic stage in the normal-phase system ethyl acetate, or c) useful extract fraction 2 is subjected by means of simulated moving bed technique in a reverse-phase system acetonitrile/water to a second chromatographic stage, and useful raffinate fraction 1 is subjected to a second chromatographic stage in the normal-phase system ethyl acetate.

4. The process according to claim 1 or 3, wherein the second chromatographic stage is carried out in the reverse-phase system acetonitrile/water using an acetonitrile/water ratio of 40:60 to 80:20 (v/v).

5. The process according to claim 4, wherein the ratio is 60:40.

6. The process according to claim 1 or 3, wherein columns and eluents during the simulated moving bed step are kept in the temperature range from 40 to 80° C.

7. The process according to claim 6, wherein the temperature is 60° C.

8. The process according to claim 1 or 3, wherein the pH of the eluent in the reverse-phase system acetonitrile/water is between 2 and 5.

9. The process according to claim 8 wherein the pH is 3.

* * * * *